United States Patent [19]

Beu

[11] 4,218,205
[45] Aug. 19, 1980

[54] THREE-SECTION SELF-SEALING DENTAL FLASK

[75] Inventor: Richard A. Beu, Eggertsville, N.Y.

[73] Assignee: Teledyne Hanau Division of Teledyne, Inc., Buffalo, N.Y.

[21] Appl. No.: 952,720

[22] Filed: Oct. 19, 1978

[51] Int. Cl.² .................... B29D 31/00; B29C 1/16; A61C 13/08
[52] U.S. Cl. .................................. 425/180; 425/179; 249/165
[58] Field of Search ............... 425/175, 176, 177, 178, 425/179, 180; 249/163, 165

[56] References Cited

U.S. PATENT DOCUMENTS

| 283,487 | 8/1883 | Housel | 425/180 |
|---|---|---|---|
| 715,182 | 12/1902 | Waegel | 425/180 |
| 1,875,596 | 9/1932 | Hazeltine | 425/180 X |
| 1,875,660 | 9/1932 | Rodin et al. | 425/178 |
| 1,926,508 | 9/1933 | Ballard | 425/180 X |
| 2,102,266 | 12/1937 | Handler | 425/178 |
| 2,359,152 | 9/1944 | Pryor et al. | 425/180 X |
| 2,660,758 | 12/1953 | Hennike et al. | 425/178 |
| 3,056,166 | 10/1962 | Weinberg | 249/163 X |
| 3,988,094 | 10/1976 | McGowan | 425/175 |
| 4,013,259 | 3/1977 | Tryon | 425/180 X |

*Primary Examiner*—J. Howard Flint, Jr.
*Attorney, Agent, or Firm*—Raymond F. Kramer

[57] ABSTRACT

A dental flask for use in molding full dentures includes bottom, middle and cover sections capable of being sealed together, either by screws for holding the bottom and cover sections to the middle section by screwing into threaded means in the middle section, or by external compressing means. The flask is of such a structure as to promote even transfer of heat to a synthetic organic polymeric plastic material for gum and palate portions of the denture and to teeth to be held thereby, and internally threaded sealing means are so located at sides of the flask as to apply sealing forces effectively and evenly when cover and bottom screws are tightened and are so located as not to interfere with molding of the denture or heat transfer to the plastic portion thereof during molding.

14 Claims, 8 Drawing Figures

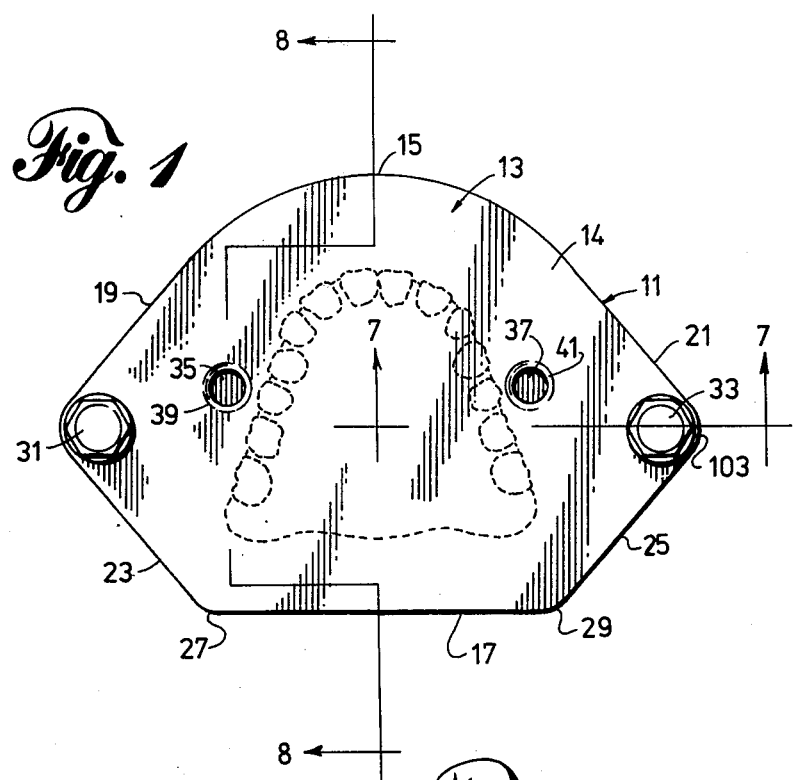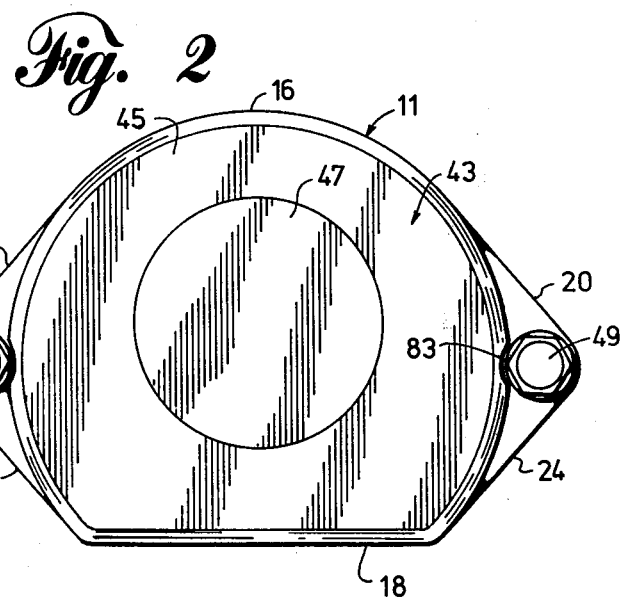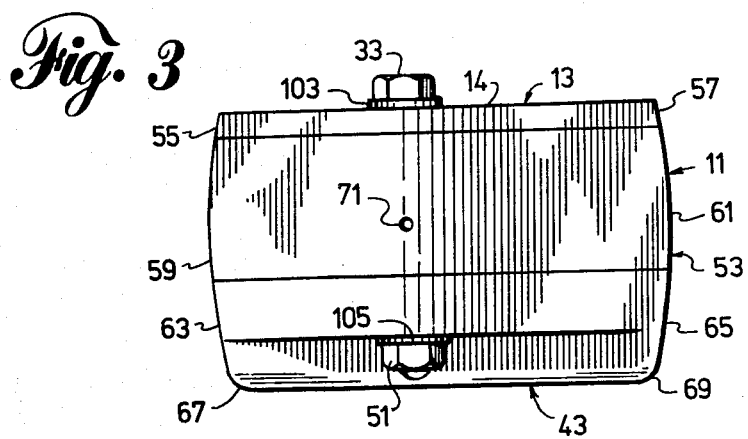

THREE-SECTION SELF-SEALING DENTAL FLASK

This invention relates to a dental flask. More particularly, it relates to a three-section, self-sealing dental flask of a structure which allows for good heat transfer to materials of a full denture being molded therein and also allows for satisfactory even application of compressing forces to seal the mold, whether such forces are applied by an external press or by screw means which are parts of the flask.

Dental flasks or molds useful in the manufacture of dentures have been in use for over a hundred years. With the discovery and commercialization of synthetic organic polymeric materials (plastics) it became possible for the molding of such materials to simulate gum and palate portions for attachment to the human gums and palate and for tight and accurate holding of the teeth in place on the synthetic gums. With the inventions and productions of articulating mechanisms it became possible for the location of artificial teeth in dentures to be scientifically determined for best manufacture of dentures and most comfortable installation thereof in the human mouth. So that the advantages of accurate articulation and natural looking plastic materials could be best obtained various types of dental flasks have been manufactured in which accurate reproduction of gum and/or palate forms holding artificial teeth could be obtained. Among the more successful of such flasks has been the three-section, ejector type flask marketed by the Hanau division of Teledyne Dental, which is a division of Teledyne, Inc. Such flask has been marketed under the trademark VARSITY by such company and by its predecessor company, Hanau Engineering Co. Inc. That flask was intended for use with an external press for holding it closed and consequently, while it possessed pins on the middle section thereof for registration with openings in the bottom and cover, it was not self-sealing (because an external press was required). Also, the positioning pins were positioned so that if screws had been located there instead uneven compressive forces for sealing the flask would have been obtained.

In addition to the mentioned commercial flask various other dental flasks have also been invented, patented and commercialized. In search of the prior art U.S. patents in the classified files of the U.S. Patent and Trademark Office, which search was conducted in Class 425, Subclasses 175, -176, -177, -178, -179 and -180, there were found the following patents, which are considered to be of interest and hereby are drawn to the attention of the Patent Examiner: U.S. Pat. Nos. 255,098; 715,182; 1,331,193; 1,595,525; 1,639,404; 1,647,048; 1,862,699; 1,875,596; 1,926,508; 2,102,266; 2,159,437; 2,359,152; and 3,988,094. Although such patents show externally compressed sealed flasks and self-sealing flasks of various types and illustrate pin means for aligning flask sections and screw means for holding such sections together they do not describe or suggest flasks suitable for both external compression sealing and self-sealing wherein aligning "pin" and threaded holding means utilize common structure. Also, they do not show the structure of the present flask, wherein the back is rounded, the front is essentially flat and threaded sealing means are located as described at the sides of the middle section to hold bottom and cover sections to it upon the tightening of appropriate cap screws, so that balanced and even pressures are transmitted to the sealing surfaces of the flask parts. Thus, this invention possesses significant advantages over the prior art dental flasks.

In accordance with the present invention a three-section, self-sealing dental flask comprises a bottom section having an upper sealing surface, a middle section having upper and lower sealing surfaces and a cover section having a lower sealing surface, each of which sections has a substantially flat front and a rounded back and which sections, when assembled, form a molding cavity for a full denture, and sealing means at two sides of the flask middle section which, in conjunction with tightening screws, are capable of applying compressive sealing forces on the bottom and cover sections of the flask when said screws are tightened so as to seal such flask with the sealing surfaces of the middle section thereof in sealing contact with corresponding sealing surfaces of the bottom and cover sections. The mentioned sealing means most desirably include internally threaded means which act as aligning means only, when a press is utilized to seal the flask.

The invention will be readily understood by reference to this description, together with the accompanying drawing, in which:

FIG. 1 is a top plan view of the assembled and sealed dental flask of this invention;

FIG. 2 is a bottom plan view thereof, rotated 180°;

FIG. 3 is a right side elevation thereof;

Figure 4:
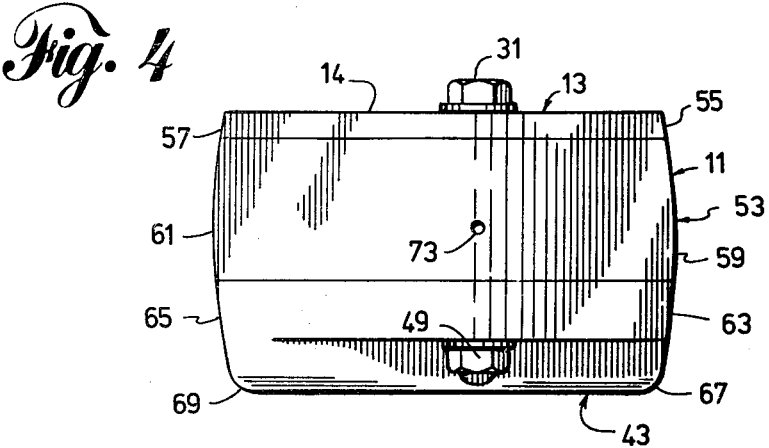
FIG. 4 is a left side elevation thereof.

In FIG. 1 dental flask 11 is shown with cover section 13 thereof including a rounded back portion 15 in the form of an arc of a circle, a substantially flat front portion 17, straight sided side portions 19 and 21, approximately tangent to the circular curve of back portion 15 and substantially straight sided side portions 23 and 25. Portions 23 and 25 are connected to front 17 at rounded corners 27 and 29. At the sides of the flask cover are shown cap screws 31 and 33, the threaded portions of which (not illustrated in FIG. 1) fit into internally threaded portions in sealing means, not illustrated in FIG. 1 but shown clearly in FIG. 7. Sides 23 and 25 are at about the same angle with respect to a center line drawn between the centers of cap screws 31 and 33 (and the mentioned sealing means) and extending beyond them, as sides 19 and 21 make with such center line. Such angle, as illustrated is between 45° and 60°, about 50°. Cover 13 has openings 35 and 37 therein for extrusion through them of mold material, e.g., gypsum cement, during the closing of the flask and during formation of the desired mold about a model of the gums and/or palate, with the artificial teeth installed in the gums. It will be noted that because of such extrusion of the mold material (and hardening thereof) outwardly directed or flaring walls 39 and 41 and the hardened extruded mold material will act to hold cover 13 in place even when screws 31 and 33 are disconnected and yet, will allow easy removal of the cover from the mold, when that is desired, by breaking the molding material which will be filling openings 35 and 37. An elevational view of walled opening 35 and flared wall 39 is shown in FIG. 8 and opening 37 and wall 41 are of the same construction.

In FIG. 2 is shown bottom section 43 of dental flask 11. As will be apparent from a comparison of FIG'S. 1 and 2 the curvatures of the cover and bottom section back portions 15 and 16 are about the same, as are the lengths and angles of the flat front and side sections 17 and 18, 19 and 20, 21 and 22, 23 and 24 and 25 and 26, respectively. Bottom section 43 includes an outer bottom portion 45 and an inner knock-out portion 47, additional details of which are shown in FIG'S. 7 and 8. Cap screws 49 and 51 for holding the flask bottom section to the middle section, as shown in FIG'S. 3-7, are located coaxially with screws 31 and 33, respectively, since the internal threaded means for screws 31 and 49 and 33 and 51, respectively, include coaxial internal threads.

FIG'S. 3 and 4, illustrating side views of the assembled and sealed flask, include cover, middle and bottom sections 13, 53 and 43, respectively, with cover screws 31 and 33 and bottom screws 49 and 51. As will be apparent, the respective front and rear surfaces 55 and 57 of the flask cover section, 59 and 61 of the flask middle section and 63 and 65 of the flask bottom section are rounded in continuous rather flat curves and the corners between such surfaces and the bottom surface 45 of the bottom section 43 are similarly rounded, as shown at 67 and 69. Drive pins 71 and 73 hold in place internally threaded sealing means, which will be described in more detail when reference is made to FIG. 7.

Figure 5:
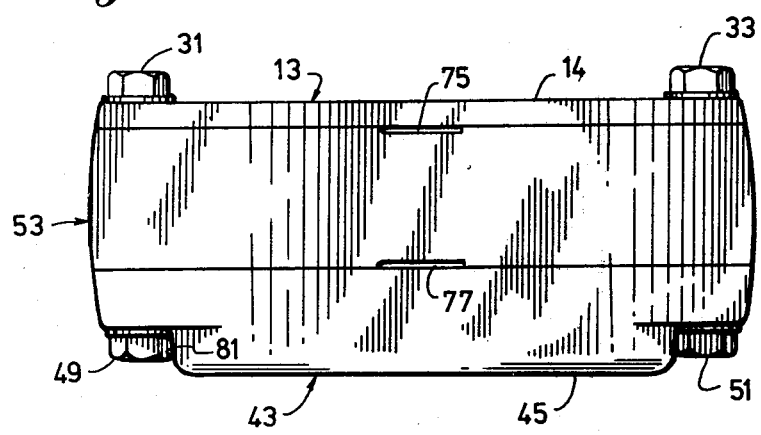
FIG. 5 is a front elevation thereof.
Figure 6:
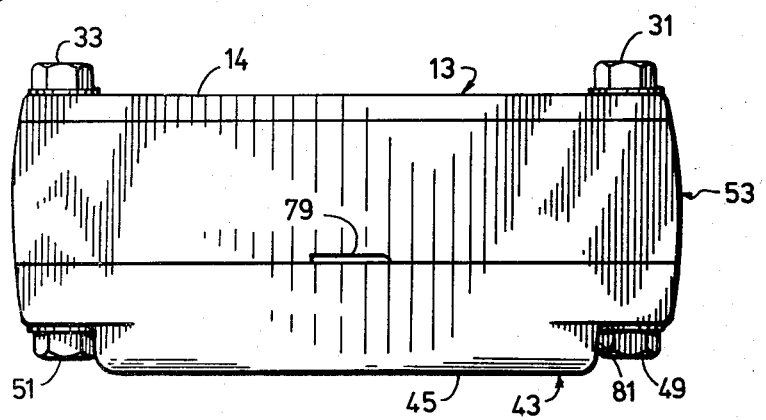
FIG. 6 is a rear elevation thereof.

In FIG. 5, a front elevational view of the present dental flask, in addition to the component parts previously described, there are also shown walled flat openings 75 and 77 in flask middle section 53. Such openings are for application of a pry or a pair of pries for opening the mold, when desired and such opening may be effected with or without the assistance of an apparatus for holding the flask parts and for facilitating application of prying leverage to them to separate them. In FIG. 6 a similar pry opening 79 in the back of the flask middle section is illustrated. In both FIG'S. 5 and 6 it is notable that the side walls, like the front and back walls of FIG'S. 3 and 4, are gentle or flat curves. It will be noted in FIG'S. 5 and 6, as well as in FIG'S. 3 and 4, that cap screws 31 and 33 project above the flask cover section top surface 14 but that cap screws 49 and 51 are above flask bottom section surface 45 and hence do not project beyond such surface, thereby allowing the sealed flask to be rested on the flat surfaces 45 and 47 of bottom 43. Between cap screw 49 and wall 81 of flask bottom section 43 is a clearance 83, shown in FIG. 2, so that the cap screw may be tightened or loosened by means of a nut driver or socket wrench, the wall of which occupies the clearance. A similar clearance 85 exists between screw 51 and corresponding wall 87 of the flask bottom section adjacent to it, as is shown in FIG. 7.

Figure 7:
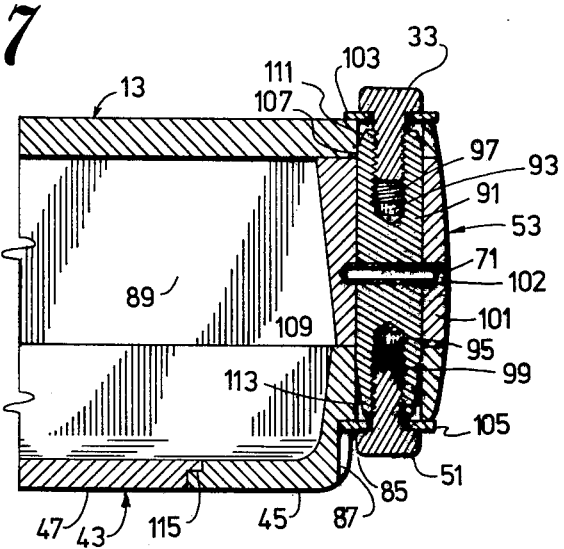
FIG. 7 is a sectional elevation of a symmetrical half of the assembled and sealed dental flask taken along plane 7—7 of FIG. 1.
Figure 8:
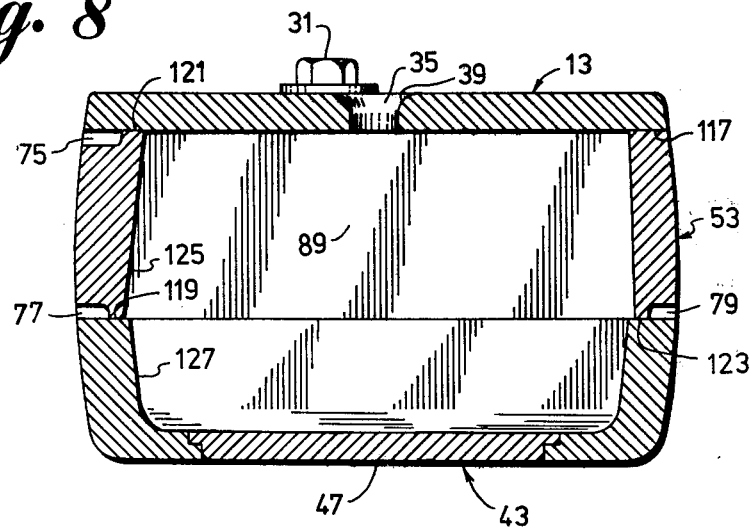
FIG. 8 is a sectional elevation thereof taken along viewing planes along the path shown by 8—8 of FIG. 1.

In FIG. 7 is shown half of an assembled sealed flask of this invention, the omitted half being a mirror image of that shown. The joinder and sealing of the cover, middle and bottom sections creates an interior volume 89 in which a cement, gypsum or other suitable internal mold may be constructed, in which molding of the denture may be effected. In a vertical cylindrical bore in middle section 53 at a side thereof (such bore is not more specifically indicated in the drawing because it is filled with the internally threaded sealing means, to be described) is positioned cylindrically walled sealing means 91, with an upper opening 93 and a lower opening 95 therein, each of which, initially cylindrical bores, are internally threaded, as indicated at 97 and 99. The sealing means is held in place at the side of the middle section by drive pin 71, driven through a transverse cylindrical opening or bore in the sealing means body and corresponding bores in the wall portion 101 of the flask middle section, as at 102. As shown, cap screws 33 and 51 are tightened into the internally threaded sealing means 91 and thereby hold flask cover and bottom sections 13 and 43 to middle section 53. Washers 103 and 105 are shown, which are spot welded to cap screws 33 and 51, respectively, to facilitate even better holding of the cover and bottom sections to the flask middle section in alignment. When the cap screws are removed it is noted that end portions 107 and 109 of the sealing means 91, which closely fit corresponding walled openings in the flask cover and bottom cover, respectively, will align the flask parts accurately, promoting the obtaining of a good seal between contacting surfaces thereof during compression of the flask parts, whether by self-sealing means or by an external press. To facilitate easy assembling of the cover and bottom sections to the flask middle section, sealing means 91 includes terminal tapered portions 111 at the upper end thereof and 113 at the lower end thereof. In FIG. 7 there is also illustrated knock-out plate 47, which is stepped at 115 so that it may rest on a corresponding ledge of flask bottom 43 and fit such bottom so that the knock-out part may only be moved inwardly, into the flask, so as to help release molding material in the bottom of the flask, after molding, when such release is desirable.

In FIG. 8 details of mold material escape opening 35 are shown, including flaring or countersunk exit portion 39 thereof. Also shown in that figure are other details of pry openings 75, 77 and 79, and knock-out plate 47. Also, cover sealing surface 117, bottom sealing surface 119 and upper and lower middle section sealing surfaces 121 and 123 are specifically indicated, as are the middle section and bottom section inner walls 125 and 127.

The materials of construction of the present flask are preferably brass for the main flask sections, stainless steel for the cap screws, washers and sealing means, and corrosion resistant steel for the drive pin or roll pin. The main mold sections are preferably forged and of yellow brass alloy although navy brass and other brasses and metals known to be suitable flask materials may also be employed. The knock-out disk may be brass sheet, cut or punched and machined to shape. The sealing means or internally threaded inserts for the flask middle section will preferably be of AISI type 316 stainless steel, the cap screws and washers will be of the same stainless steel and the drive or roll pin will preferably be of AISI type 420 corrosion resistant steel.

The various dimensions of the present flask will depend to some extent on the particular materials being molded. For its main intended purpose, that of holding a mold for artificial full dentures for human use, the flask wall thicknesses will be sufficient to withstand normal pressures which may be applied to the mold, e.g., 3 to 70 kg./sq. cm., and small enough so as rapidly to transmit external temperatures to the flask, as during curing of acrylic or other polymers in a cement or gypsum mold. Similarly, the dimensions of the flask will be such that prohibitively long times will not be required for heat transfer to and from the interior of the mold through the molding material. Normally the wall thicknesses will be in the range of 0.5 to 1.5 cm. and cover and bottom thicknesses will be from 0.1 to 0.6 cm. The flask itself will normally be from 4 to 8 cm. high, exclusive of the projecting cap screws and washers, preferably 6 to 7 cm. high, 12 to 17 cm. wide, preferably 14 to 15 cm. wide, and 9 to 12 cm. deep (measurement transverse to width), preferably 9.5 to 11 cm. deep.

So as to obtain satifactorily uniform applications of flask closing pressures and good sealing of the flask, as well as good heat transfer to the interior thereof from an external source, the threaded sealing means will be located outside the central ⅔ of the length (elsewhere sometimes referred to as width) of the flask middle section (which is usually measured along a center line between centers of the sealing means). Preferably the threaded means will be located outside the center ¾ of such length. Also, for better distribution of sealing forces and pressures and for tighter seals between the peripheral sealing surfaces, so that they may be tightly held together with no leakage of plastic molding material through them when closed, such center line between centers of the threaded sealing means will be at a distance from 35 to 70% of the distance from the front surface of the substantially flat front of the flask middle section to the backmost surface of the rounded back of such section. The center line divides the area of the flask middle section so that the portion in front of the center line is from 40 to 60% of such total area. Preferably, the mentioned center line will be at a distance from 40 to 60% of the distance from the front to back of the flask middle section and will divide the area so that the portion in front of the center line is 45 to 55% of such total area. The distances and areas mentioned include the wall thicknesses of the flask middle section but the percentages mentioned are also usually applicable when wall thicknesses are neglected.

The advantages of the present invention have been referred to previously but will now be described in more detail. First, the flask is of such structure as to facilitate easy construction of a suitable mold therein in which a prosthesis for holding artificial teeth in a human mouth can be accurately produced. The structures of the flask and the contained mold facilitate even heat transfer to material being cured (or fused) therein, obviating stresses which can subsequently distort dentures in use and can lead to discomfort by their wearers. The substantially flat shape of the front, as well as of the bottom, facilitates storage and racking of assembled flasks. The presence of the sealing means at the sides of the flask, when utilized with screws or other holding means adapted to hold a cover plate and a bottom section to the sealing means, provides for even distribution of holding pressure to the flask parts and tends to prevent any uneven contacting of sealing surfaces, which might otherwise result in objectionable leakages. The flasks are self-sealing and yet, because the sealing means do not project beyond the cover and bottom sections, are adaptable for use with external compressive means, such as may be desirable when several flasks may be compressed at one time in series positioning in a press. In addition to helping to equalize the application of pressure to the mold parts by location of the sealing means substantially centrally at the sides, as described, the greater mass of metal near the sealing means at the sides does not interfere with even heat transfer to denture materials being cured (or being cooled). Due to the positioning of the denture in the mold in the flask the main surfaces thereof, the portion of the gum holding the front teeth and the palate portions, are away from the sealing means and consequently, heat transfer to them is primarily through the rounded and substantially flat portions of the flask and the relatively even walled mold therein.

In use, the present flask is employed in essentially the same manner as has been described in the literature for operating the Varsity ejector type flask previously mentioned, except for the self-sealing applications of the present flask described herein. Accordingly, preparation of the wax form with teeth embedded therein, making of the mold from such form, removal of the wax and molding of a synthetic organic polymeric plastic, preferably an acrylic polymer, denture need not be described in detail in this application.

It will be evident to one of skill in the art that various equivalents and substitutes may be employed without departing from the present invention. For example, instead of utilizing cap screws, set screws turnable by Allen wrenches may be employed and other sealing means than internally threaded means may be substituted to hold the flask parts together when desired. For example, toggle and other suitable clamps could be substituted and parts of such clamps could be built into one or more of the flask sections. Mold shapes could be varied somewhat to more closely approximate denture shapes or the shapes of other prostheses which could be molded in the present apparatuses. Instead of brass, stainless steel and corrosion resistant steel, other materials of construction could be employed, including, in some instances, synthetic organic polymers, especially those which are fiber reinforced. However, those materials previously mentioned are highly preferred, for their durability, machinability, thermal conductivity and strength and the structures described are considered to be superior and at present are the preferred embodiments of this invention.

What is claimed is:

1. A three-section, self-sealing dental flask which comprises a bottom section having an upper sealing surface, a middle section having upper and lower sealing surfaces and a cover section having a lower sealing surface, each of which sections has a substantially flat front and a rounded back and which sections, when assembled, form a molding cavity for a full denture, and sealing means at two sides of the flask middle section which, in conjunction with tightening screws, are capable of applying compressive sealing forces on the bottom and cover sections of the flask when said screws are tightened so as to seal such flask with the sealing surfaces of the middle section thereof in sealing contact with corresponding sealing surfaces of the bottom and cover sections.

2. A dental flask according to claim 1 wherein the sealing means at the sides of the middle section thereof include internally threaded means at both such sides, adapted for having separate bottom holding and cover holding screws tightened therein to seal the flask, said threaded means being located outside the center ⅔ of the length of the flask middle section and with the center line between centers of the threaded means being located at a distance from 35 to 70% of the distance from the surface of the substantially flat front of the flask middle section to the backmost surface of the rounded back of the flask middle section so that the center line divides the area of the flask middle section, so that the portion in front of said center line is from 40 to 60% of such total area.

3. A dental flask according to claim 2 wherein the internally threaded sealing means at the sides of the flask middle section terminate short of the bottom surface of the bottom flask section and short of the top surface of the cover flask section.

4. A dental flask according to claim 3 wherein the internally threaded sealing means at the sides of the flask middle section are each long enough so as to project into walled openings in the bottom flask section and the cover flask section and the exteriors of said internally threaded sealing means and the walls of the openings in such sections are in alignment and of matching sizes so that when the bottom flask section and the cover flask section are placed against the middle flask section with the internally threaded sealing means projecting into the openings in such sections, such sections are aligned with the middle section.

5. A dental flask according to claim 4 wherein the exteriors of the internally threaded sealing means are at least partially tapered to promote ready fitting of the middle flask section to the bottom and cover flask sections of the dental flask.

6. A dental flask according to claim 5 wherein the sealing means are each integral internally threaded inserts held in vertical bores in the middle flask section by drive pins passing through such middle flask section and respective horizontal bores in said inserts.

7. A dental flask according to claim 6 having four threaded cap screws, each of which screws includes an integral washer section, holding the bottom and cover sections to the middle flask section by being screwed into the internally threaded inserts.

8. A dental flask according to claim 7 wherein the rounded back of the flask and the interior of the back portion of the flask to the center line between the threaded means are essentially arcs of a circle to encompass substantially equidistantly the teeth portion of a full denture to be molded, the front of the flask and the front of the interior thereof are substantially flat so as to be about equidistant from the toothless palate portion of the full denture to be molded, the sides of the interior of the front of the flask are substantially continuations of the curvature of the interior of the back thereof and the sides of the exterior of the flask are substantially straight walled portions with back parts of such sides being tangent to the external curvature of the back, and with front parts of such sides being of a substantially equal angle to that of the back parts with the center line and with such parts meeting in arcs which curvedly enclose the internally threaded sealing means.

9. A dental flask according to claim 8 wherein the cover includes a pair of flaring openings for expulsion of molding material during closing of the mold, the bottom includes a knock-out for separating the molding material from the bottom section after molding and the middle flask section includes a plurality of pry recesses to facilitate opening of the mold.

10. A dental flask according to claim 1 wherein the sealing means at the sides of the middle section are located outside the central ¾ of the length of the flask middle section and equidistant from the front thereof, with the center line between centers of such sealing means being from 40 to 60% of the distance from the surface of the substantially flat front to the backmost surface of the rounded back of the flask middle section, so that such center line divides the area of the flask middle section so that the portion in front of said center line is from 45 to 55% of such total area.

11. A dental flask according to claim 1 wherein the sealing means terminate short of the bottom surface of the flask bottom section and short of the top surface of the flask cover section, when the flask is assembled.

12. A dental flask according to claim 1 wherein the sealing means are internally threaded, are each long enough so as to project into openings in the flask bottom section and the flask cover section and the exteriors of said sealing means and interior walls of the openings in such sections are in alignment and of matching sizes when the flask bottom section and the flask cover section are placed against the flask middle section with the sealing means projected into the openings in such sections and such sections are aligned with the middle section.

13. A dental flask according to claim 1 wherein the rounded back of the flask and the interior of the back portion of the flask to a center line connecting the sealing means are essentially arcs of a circle to encompass substantially equidistantly the teeth portion of a full denture to be molded, the front of the flask and the front of the interior thereof are substantially flat so as to be about equidistant from a toothless palate portion of the full denture to be molded, the sides of the interior of the front of the flask are substantially continuations of the curvature of the interior of the back thereof and the sides of the exterior of the flask are substantially straight walled portions tangent to the external curvature of the back, forming a substantially matching angle with the center line for the front and meeting in an arc which curvedly encloses the sealing means.

14. A dental flask according to claim 12 having four threaded screws holding the flask bottom and cover sections to the flask middle section by being screwed into the internally threaded inserts of the middle section.

* * * * *